(12) United States Patent
Nakasugi et al.

(10) Patent No.: US 8,900,797 B2
(45) Date of Patent: Dec. 2, 2014

(54) DEVELOPABLE BOTTOM ANTI-REFLECTIVE COATING

(71) Applicants: Shigemasa Nakasugi, Kakegawa (JP); Shinji Miyazaki, Kakegawa (JP); Munirathna Padmanaban, Bridgewater, NJ (US); Alberto D. Dioses, Doylestown, PA (US)

(72) Inventors: Shigemasa Nakasugi, Kakegawa (JP); Shinji Miyazaki, Kakegawa (JP); Munirathna Padmanaban, Bridgewater, NJ (US); Alberto D. Dioses, Doylestown, PA (US)

(73) Assignee: AZ Electronic Materials (Luxembourg) S.A.R.L., Luxembourg (LU)

( * ) Notice: Subject to any disclaimer, the term of this patent is extended or adjusted under 35 U.S.C. 154(b) by 195 days.

(21) Appl. No.: 13/627,599

(22) Filed: Sep. 26, 2012

(65) Prior Publication Data

US 2014/0087311 A1  Mar. 27, 2014

(51) Int. Cl.
| | |
|---|---|
| *C07D 251/38* | (2006.01) |
| *C07D 213/69* | (2006.01) |
| *C07D 213/70* | (2006.01) |
| *C07D 239/60* | (2006.01) |
| *C07D 251/30* | (2006.01) |
| *G03F 7/004* | (2006.01) |
| *G03F 7/20* | (2006.01) |

(52) U.S. Cl.
USPC .............. 430/288.1; 430/270.1; 430/271.1; 430/311; 544/219; 544/302; 546/291; 546/296

(58) Field of Classification Search
None
See application file for complete search history.

(56) References Cited

U.S. PATENT DOCUMENTS

| | | | |
|---|---|---|---|
| 6,156,479 A | 12/2000 | Meador et al. | |
| 7,824,837 B2 | 11/2010 | Wu et al. | |
| 8,039,202 B2 | 10/2011 | Sui et al. | |
| 8,088,548 B2 | 1/2012 | Houlihan et al. | |
| 8,329,387 B2 | 12/2012 | Yao et al. | |
| 8,455,176 B2 | 6/2013 | Houlihan et al. | |
| 2005/0214674 A1* | 9/2005 | Sui et al. | 430/270.1 |
| 2010/0119972 A1* | 5/2010 | Houlihan et al. | 430/281.1 |

FOREIGN PATENT DOCUMENTS

| | | | |
|---|---|---|---|
| JP | 2008-501985 A | | 1/2008 |
| WO | WO-2005/108510 A1 * | | 11/2005 |

* cited by examiner

*Primary Examiner* — Cynthia Hamilton
(74) *Attorney, Agent, or Firm* — Sangya Jain

(57) ABSTRACT

The present invention provides a cross-linking agent capable of preventing formation of scum from a bottom anti-reflective coating, and also provides a composition for forming a bottom anti-reflection coating containing the agent. The cross-linking agent is a nitrogen-containing aromatic compound having at least one vinyloxy group or N-methoxymethylamide group, and the composition contains the cross-linking agent. The cross-linking agent of the formula (1) can be produced by reaction of a nitrogen-containing aromatic compound, a halogen compound having a vinyloxy group or N-methoxymethylamide group and a basic compound.

15 Claims, No Drawings

DEVELOPABLE BOTTOM ANTI-REFLECTIVE COATING

TECHNICAL FIELD

This invention relates to a cross-linking agent employed in lithographic pattern formation using photoresist, also to a composition containing the agent and used for forming a bottom anti-reflective coating, and still also to a bottom anti-reflective coating formation method employing the composition. In addition, the present invention further relates to a bottom anti-reflective coating formed from the composition.

BACKGROUND ART

In production of semiconductor devices, micro-fabrication is generally carried out according to lithographic techniques by use of photoresist. The process of micro-fabrication comprises: forming a thin photoresist layer on a semiconductor substrate such as a silicon wafer; covering the layer with a mask pattern corresponding to the aimed device pattern; exposing the layer to active light such as ultraviolet (UV) light through the mask pattern; developing the exposed layer to obtain a photoresist pattern; and etching the substrate by use of the photoresist pattern as a protective film, to form a fine relief corresponding to the above pattern. Since the degree of integration in semiconductor devices has been increased recently, the exposure tends to be carried out by use of light of very short wavelength, such as KrF excimer laser light (wavelength: 248 nm), ArF excimer laser light (wavelength: 193 nm) or extreme UV light (wavelength: 13.5 nm). The above photolithographic process, however, often suffers from a problem of dimension precision degradation of the photoresist pattern. The dimension precision degradation is caused by a standing wave of light reflected from the substrate and/or by diffused reflection of the exposure light due to roughness of the substrate. Further, the resist layer may be adversely affected by gases given off from the substrate placed thereunder if the exposure is performed by use of light of very short wavelength, such as extreme UV light. To cope with those problems, many researchers are studying about a bottom anti-reflective coating provided between the photoresist layer and the substrate. The bottom anti-reflective coating is required to have various properties. For example, it is preferred for the bottom anti-reflective coating to largely absorb radiation used for exposure of the photoresist, to prevent diffuse reflection and the like so that the exposed and developed photoresist can have a cross section perpendicular to the substrate surface, and to be insoluble in solvents contained in the photoresist composition (namely, not to cause intermixing). The intermixing is particularly serious because it often gives adverse effects to the interface between the photoresist layer and the bottom anti-reflective coating. Accordingly, the intermixing is liable to make it difficult to control the pattern or shape of the photoresist.

The bottom anti-reflective coating is often formed from a thermo-crosslinkable composition, so as to prevent intermixing with the photoresist applied thereon. Consequently, the formed coating is generally insoluble in a developing solution used for development of the photoresist. Accordingly, in general, the anti-reflective coating must be removed by dry-etching before fabrication of the semiconductor substrate (see, for example, Patent document 1).

However, when the coating is removed by dry-etching, the photoresist tends to be partly removed together with the coating. This makes it difficult to keep enough thickness of the photoresist to fabricate the substrate.

In view of this, it is desired to provide a bottom anti-reflective coating which is sufficiently soluble in a developing solution used for development of the photoresist and hence which can be developed and removed together with the photoresist. In order to meet this desire, researchers have studied the bottom anti-reflective coating which is developable and removable together with the photoresist.

For example, it has been studied to make hydroxyl or carboxylic acid react with vinyl ether, so as to form a bottom anti-reflective coating developable and removable together with the photoresist (Patent document 2). However, this kind of method often has a problem of scum formed from a bottom anti-reflective coating in pattern formation.

PRIOR ART DOCUMENTS

[Patent document 1] U.S. Pat. No. 6,156,479
[Patent document 2] Japanese Unexamined Patent Application Publication No. 2008-501985

DISCLOSURE OF INVENTION

Problem to be Solved by the Invention

In consideration of the above problem, it is an object of the present invention to provide a cross-linking agent enabling to prevent formation of scum from a bottom anti-reflective coating. Further, it is another object of the present invention to provide a composition enabling to form a bottom anti-reflective coating suffering less from formation of scum.

Means for Solving Problem

The present invention resides in a cross-linking agent represented by the following formula (1):

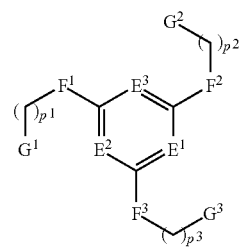

(1)

wherein
each of $E^1$ to $E^3$ is independently selected from the group consisting of carbon and nitrogen atoms, provided that at least one of them is a nitrogen atom;
each of $F^1$ to $F^3$ is independently selected from the group consisting of oxygen and sulfur atoms;
each of $G^1$ to $G^3$ is independently selected from the group consisting of a vinyloxy group, a N-methoxymethylamide group ($CONHCH_2OCH_3$) and a hydrogen atom, provided that at least one of them is a vinyloxy group or N-methoxymethylamide group; and
each of $p^1$ to $p^3$ is independently selected from integer including 0 provided that at least any two of them are at least 1 or above 1.

The present invention also resides in a process for preparing a cross-linking agent, characterized in that
a compound represented by the following formula (2):

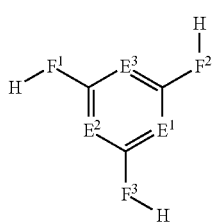
(2)

wherein each of $E^1$ to $E^3$ is independently selected from the group consisting of carbon and nitrogen atoms, provided that at least one of them is a nitrogen atom; and each of $F^1$ to $F^3$ is independently selected from the group consisting of oxygen and sulfur atoms and a compound represented by the following formula (3):

(3)

wherein X is selected from the group consisting of chlorine, bromine and iodine atoms; G is a vinyloxy group or a N-methoxymethylamide group; and p is an integer of 0 or more are made to react with a basic compound.

The present invention further resides in a composition for forming a bottom anti-reflective coating, comprising a solvent, the above cross-linking agent, and a polymer represented by the following formula (4):

$-A_m-B_n-$ (4)

wherein

A and B are repeating units represented by the following formulas (A) and (B), respectively;

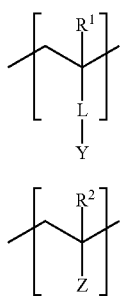

in which each of $R^1$ and $R^2$ is independently a group selected from the group consisting of a hydrogen atom and alkyl groups;

L is a linking group selected from the group consisting of a single bond, straight-chain and branched chain alkylene groups having one or more carbon atoms, and COO;

Y is an aromatic group containing one or more benzene rings, provided that the aromatic group may or may not have a substituent selected from the group consisting of alkyl, aryl, halogen atoms, alkoxy, nitro, aldehyde, cyano, amide, dialkylamino, sulfonamide, imide, carboxy, carboxylic acid ester, sulfo, sulfonic acid ester, alkylamino, and arylamino, and also provided that one of the benzene rings contained in the aromatic group may be replaced with a quinone ring; and Z is a group selected from the group consisting of $R^3COOR^4$ and $R^3OR^4$, in which $R^3$ is a group selected from the group consisting of single bond, oxygen atom, aromatic ring, and straight-chain and branched chain alkylene groups which have one or more carbon atoms (such as $C_1$ to $C_{12}$) and which may be substituted with a fluorine atom, and also in which $R^4$ is a group selected from the group consisting of a hydrogen atom, substituted hydrocarbon groups and non-substituted hydrocarbon groups;

the repeating units A and B may be connected either randomly or to form a block, each of the repeating units A and B may be a combination of two or more repeating units having different structures, and m and n are numbers indicating polymerization degrees, and are a number of 10 or more and a number of 0 or more, respectively.

The present invention furthermore resides in a bottom anti-reflective coating obtained by casting onto a substrate the above composition for forming a bottom anti-reflective coating, and then heating it.

The present invention yet further resides in a pattern formation method comprising:

casting the above composition for forming a bottom anti-reflective coating onto a semiconductor substrate, and then baking it to form a bottom anti-reflective coating;

forming a photoresist layer on the bottom anti-reflective coating;

subjecting to exposure the semiconductor substrate covered with the bottom anti-reflective coating and the photoresist layer; and developing the exposed substrate with a developing solution.

Effect of the Invention

The composition according to the present invention enables to prevent intermixing with a photoresist composition layer and thereby to form a resist pattern having a cross section perpendicular to the substrate surface. Further, by use of the composition of the present invention for forming a bottom anti-reflective coating, it becomes possible to avoid both formation of scum and loss of bias between isolated and dense lines and also to form a bottom anti-reflective coating which can be developed and removed together with the photoresist.

BEST MODE FOR CARRYING OUT THE INVENTION

Embodiments of the present invention are described below in detail.

[Cross-Linking Agent Having a Nitrogen-Containing Aromatic Ring]

The cross-linking agent according to the present invention is advantageously used in a lithographic composition, particularly, in a composition for forming a bottom anti-reflective coating. The structure thereof can be represented by the following formula (1):

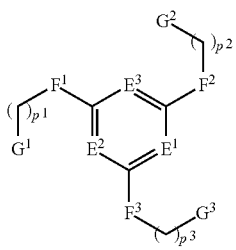

(1)

wherein each of $E^1$ to $E^3$ is independently selected from the group consisting of carbon and nitrogen atoms, provided that at least one of them is a nitrogen atom;

each of $F^1$ to $F^3$ is independently selected from the group consisting of oxygen and sulfur atoms;

each of $G^1$ to $G^3$ is independently selected from the group consisting of a vinyloxy group, a N-methoxymethylamide group and a hydrogen atom, provided that at least one of them is a vinyloxy group or a N-methoxymethylamide group; and each of $p^1$ to $p^3$ is independently selected from integer including 0 provided that at least any two of them are at least 1 or above 1.

Similarly to known cross-linking agents, the cross-linking agent according to the present invention has a function of reacting with a polymer or the like to promote hardening of the composition. The cross-linking agent of the present invention contains at least one vinyloxy group as a reactive group. Actually, in the formula (1), at least one of $G^1$ to $G^3$ is a vinyloxy group or a N-methoxymethylamide group. The vinyloxy group enables crosslinking with carboxyl groups and/or phenolic hydroxyl groups contained in the polymer. Especially, in case of the vinyloxy group, this means that the vinyloxy group forms an acetal bond with a carboxyl group or a phenolic hydroxyl group contained in the polymer. The acetal bond is cleaved by an acid formed from a photo acid generator described later or by moisture in air or in a developing solution.

The atoms $F^1$ to $F^3$ in the formula (1) have a function of making it easy to synthesize the cross-linking agent. Although the cross-linking reaction occurs and proceeds even if all the atoms $F^1$ to $F^3$ are carbon atoms, it is difficult to synthesize that cross-linking agent itself.

Each of the integers $p^1$ to $p^3$ indicates length of a linking group between the aromatic ring and the vinyloxy group or the N-methoxymethylamide group as a reactive groups. If the linking group is too long, it is often difficult to achieve sufficient hardening. On the other hand, however, if the linking group is too short, it is often difficult to achieve sufficient cross-linking. Accordingly, at least two of the integers $p^1$ to $p^3$ must be not less than 1, and each of them is preferably 2 to 10, more preferably 4 to 10. In one embodiment $E^1$ to $E^3$ are nitrogen or only 2 of $E^1$ to $E^3$ are nitrogen or only 1 of $E^1$ to $E^3$ is nitrogen. In another embodiment $F^1$ to $F^3$ are oxygen and in another embodiment $F^1$ to $F^3$ are sulfur. In one embodiment $G^1$ to $G^3$ are vinyloxy groups and in another embodiment $G^1$ to $G^3$ are N-methoxymethylamide groups.

Examples of the cross-linking agent represented by the formula (1) include:

sulfur-containing compounds, such as,
2,4,6-tris((vinyloxy)thio)-1,3,5-triazine,
2,4,6-tris(((vinyloxy)methyl)thio)-1,3,5-triazine,
2,4,6-tris(((vinyloxy)ethyl)thio)-1,3,5-triazine,
2,4,6-tris(((vinyloxy)propyl)thio)-1,3,5-triazine,
2,4,6-tris(((vinyloxy)butyl)thio)-1,3,5-triazine,
2,4,6-tris(((vinyloxy)pentyl)thio)-1,3,5-triazine,
2,4,6-tris(((vinyloxy)hexyl)thio)-1,3,5-triazine,
2,4,6-tris(((2-vinyloxy)methyl)thio)pyrimidine,
2,4,6-tris(((2-vinyloxy)ethyl)thio)pyrimidine,
2,4,6-tris(((3-vinyloxy)propyl)thio)pyrimidine,
2,4,6-tris(((3-vinyloxy)butyl)thio)pyrimidine,
2,4,6-tris(((3-vinyloxy)pentyl)thio)pyrimidine,
2,4,6-tris(((3-vinyloxy)hexyl)thio)pyrimidine,
4,6-bis((2-(vinyloxy)methyl)thio)pyrimidine,
4,6-bis((2-(vinyloxy)ethyl)thio)pyrimidine,
4,6-bis((2-(vinyloxy)propyl)thio)pyrimidine,
4,6-bis((2-(vinyloxy)butyl)thio)pyrimidine,
4,6-bis((2-(vinyloxy)pentyl)thio)pyrimidine,
4,6-bis((2-(vinyloxy)hexyl)thio)pyrimidine,
2,4-bis((2-(vinyloxy)methyl)thio)pyrimidine,
2,4-bis((2-(vinyloxy)ethyl)thio)pyrimidine,
2,4-bis((2-(vinyloxy)propyl)thio)pyrimidine,
2,4-bis((2-(vinyloxy)butyl)thio)pyrimidine,
2,4-bis((2-(vinyloxy)pentyl)thio)pyrimidine,
2,4-bis((2-(vinyloxy)hexyl)thio)pyrimidine,
2,3-bis((2-(vinyloxy)methyl)thio)pyridine,
2,3-bis((2-(vinyloxy)ethyl)thio)pyridine,
2,3-bis((2-(vinyloxy)butyl)thio)pyridine,
2,3-bis((2-(vinyloxy)pentyl)thio)pyridine,
2,3-bis((2-(vinyloxy)hexyl)thio)pyridine,
2,4-bis((2-(vinyloxy)methyl)thio)pyridine,
2,4-bis((2-(vinyloxy)ethyl)thio)pyridine,
2,4-bis((2-(vinyloxy)butyl)thio)pyridine,
2,4-bis((2-(vinyloxy)pentyl)thio)pyridine,
2,4-bis((2-(vinyloxy)hexyl)thio)pyridine,
2,5-bis((2-(vinyloxy)methyl)thio)pyridine,
2,5-bis((2-(vinyloxy)ethyl)thio)pyridine,
2,5-bis((2-(vinyloxy)butyl)thio)pyridine,
2,5-bis((2-(vinyloxy)pentyl)thio)pyridine,
2,5-bis((2-(vinyloxy)hexyl)thio)pyridine,
2,6-bis((2-(vinyloxy)methyl)thio)pyridine,
2,6-bis((2-(vinyloxy)ethyl)thio)pyridine,
2,6-bis((2-(vinyloxy)butyl)thio)pyridine,
2,6-bis((2-(vinyloxy)pentyl)thio)pyridine,
2,6-bis((2-(vinyloxy)hexyl)thio)pyridine;
2,2',2''-((1,3,5-triazine-2,4,6-triyl)tris(sulfanediyl))tris(N-methoxyacetamide),
3,3',3''-((1,3,5-triazine-2,4,6-triyl)tris(sulfanediyl))tris(N-methoxypropanamide),
4,4',4''-((1,3,5-triazine-2,4,6-triyl)tris(sulfanediyl))tris(N-methoxybutaneamide),
5,5',5''-((1,3,5-triazine-2,4,6-triyl)tris(sulfanediyl))tris(N-methoxypentaneamide),
6,6',6''-((1,3,5-triazine-2,4,6-triyl)tris(sulfanediyl))tris(N-methoxyhexaneamide),
2,2',2''-(pyrimidine-2,4,6-triyltris(sulfanediyl))tris(N-methoxyacetamide),
3,3',3''-(pyrimidine-2,4,6-triyltris(sulfanediyl))tris(N-methoxypropanamide),
4,4',4''-(pyrimidine-2,4,6-triyltris(sulfanediyl))tris(N-methoxybutaneamide),
5,5',5''-(pyrimidine-2,4,6-triyltris(sulfanediyl))tris(N-methoxypentaneamide),
6,6',6''-(pyrimidine-2,4,6-triyltris(sulfanediyl))tris(N-methoxyhexaneamide),
2,2'-(pyrimidine-2,4-diylbis(sulfanediyl))bis(N-methoxyacetamide),
3,3'-(pyrimidine-2,4-diylbis(sulfanediyl))bis(N-methoxypropaneamide),
4,4'-(pyrimidine-2,4-diylbis(sulfanediyl))bis(N-methoxybutaneamide), 5,5'-(pyrimidine-2,4-diylbis(sulfanediyl))bis(N-methoxypentaneamide),
6,6'-(pyrimidine-2,4-diylbis(sulfanediyl))bis(N-methoxyhexaneamide),
2,2'-(pyrimidine-4,6-diylbis(sulfanediyl))bis(N-methoxyacetamide),
3,3'-(pyrimidine-4,6-diylbis(sulfanediyl))bis(N-methoxypropanamide),
4,4'-(pyrimidine-4,6-diylbis(sulfanediyl))bis(N-methoxybutaneamide),
5,5'-(pyrimidine-4,6-diylbis(sulfanediyl))bis(N-methoxypentaneamide),
6,6'-(pyrimidine-4,6-diylbis(sulfanediyl))bis(N-methoxyhexaneamide),
2,2'-(pyridine-2,3-diylbis(sulfanediyl))bis(N-methoxyacetamide),
3,3'-(pyridine-2,3-diylbis(sulfanediyl))bis(N-methoxypropaneamide),
4,4'-(pyridine-2,3-diylbis(sulfanediyl))bis(N-methoxybutaneamide),
5,5'-(pyridine-2,3-diylbis(sulfanediyl))bis(N-methoxypentaneamide),
6,6'-(pyridine-2,3-diylbis(sulfanediyl))bis(N-methoxyhexaneamide),
2,2'-(pyridine-2,4-diylbis(sulfanediyl))bis(N-methoxyacetamide),
3,3'-(pyridine-2,4-diylbis(sulfanediyl))bis(N-methoxypropaneamide),
4,4'-(pyridine-2,4-diylbis(sulfanediyl))bis(N-methoxybutaneamide),
5,5'-(pyridine-2,4-diylbis(sulfanediyl))bis(N-methoxypentaneamide),
6,6'-(pyridine-2,4-diylbis(sulfanediyl))bis(N-methoxyhexaneamide),
2,2'-(pyridine-2,5-diylbis(sulfanediyl))bis(N-methoxyacetamide),
3,3'-(pyridine-2,5-diylbis(sulfanediyl))bis(N-methoxypropaneamide),
4,4'-(pyridine-2,5-diylbis(sulfanediyl))bis(N-methoxybutaneamide),
5,5'-(pyridine-2,5-diylbis(sulfanediyl))bis(N-methoxypentaneamide),
6,6'-(pyridine-2,5-diylbis(sulfanediyl))bis(N-methoxyhexaneamide),
2,2'-(pyridine-2,6-diylbis(sulfanediyl))bis(N-methoxyacetamide),
3,3'-(pyridine-2,6-diylbis(sulfanediyl))bis(N-methoxypropaneamide),
4,4'-(pyridine-2,6-diylbis(sulfanediyl))bis(N-methoxybutaneamide),
5,5'-(pyridine-2,6-diylbis(sulfanediyl))bis(N-methoxypentaneamide), and
6,6'-(pyridine-2,6-diylbis(sulfanediyl))bis(N-methoxyhexaneamide),
and
oxygen-containing compounds, such as,
2,4,6-tris(vinylperoxy)-1,3,5-triazine,
2,4,6-tris((vinyloxy)methoxy)-1,3,5-triazine,
2,4,6-tris((vinyloxy)ethoxy)-1,3,5-triazine,
2,4,6-tris((vinyloxy)propoxy)-1,3,5-triazine,
2,4,6-tris((vinyloxy)butoxy)-1,3,5-triazine,
2,4,6-tris((vinyloxy)pentoxy)-1,3,5-triazine,
2,4,6-tris((vinyloxy)hexoxy)-1,3,5-triazine,
2,4,6-tris(2-(vinyloxy)methoxy)pyrimidine,
2,4,6-tris(2-(vinyloxy)ethoxy)pyrimidine,
2,4,6-tris(2-(vinyloxy)propoxy)pyrimidine,
2,4,6-tris(2-(vinyloxy)butoxy)pyrimidine,
2,4,6-tris(2-(vinyloxy)pentoxy)pyrimidine,
2,4,6-tris(2-(vinyloxy)hexoxy)pyrimidine,
4,6-bis(2-(vinyloxy)methoxy)pyrimidine,
4,6-bis(2-(vinyloxy)ethoxy)pyrimidine,
4,6-bis(2-(vinyloxy)propoxy)pyrimidine,
4,6-bis(2-(vinyloxy)butoxy)pyrimidine,
4,6-bis(2-(vinyloxy)pentoxy)pyrimidine,
4,6-bis(2-(vinyloxy)hexoxy)pyrimidine,
2,4-bis(2-bis(2-(vinyloxy)methoxy)pyrimidine,
2,4-bis(2-bis(2-(vinyloxy)ethoxy)pyrimidine,
2,4-bis(2-bis(2-(vinyloxy)propoxy)pyrimidine,
2,4-bis(2-bis(2-(vinyloxy)butoxy)pyrimidine,
2,4-bis(2-bis(2-(vinyloxy)pentoxy)pyrimidine,
2,4-bis(2-bis(2-(vinyloxy)hexoxy)pyrimidine,
2,3-bis((2-vinyloxy)methoxy)pyridine,
2,3-bis((2-vinyloxy)ethoxy)pyridine,
2,3-bis((2-vinyloxy)butoxy)pyridine,
2,3-bis((2-vinyloxy)pentoxy)pyridine,
2,3-bis((2-vinyloxy)hexoxy)pyridine,
2,4-bis((2-vinyloxy)methoxy)pyridine,
2,4-bis((2-vinyloxy)ethoxy)pyridine,
2,4-bis((2-vinyloxy)butoxy)pyridine,
2,4-bis((2-vinyloxy)pentoxy)pyridine,
2,4-bis((2-vinyloxy)hexoxy)pyridine,
2,5-bis((2-vinyloxy)methoxy)pyridine,
2,5-bis((2-vinyloxy)ethoxy)pyridine,
2,5-bis((2-vinyloxy)butoxy)pyridine,
2,5-bis((2-vinyloxy)pentoxy)pyridine,
2,5-bis((2-vinyloxy)hexoxy)pyridine,
2,6-bis((2-vinyloxy)methoxy)pyridine,
2,6-bis((2-vinyloxy)ethoxy)pyridine,
2,6-bis((2-vinyloxy)butoxy)pyridine,
2,6-bis((2-vinyloxy)pentoxy)pyridine,
2,6-bis((2-vinyloxy)hexoxy)pyridine,
2,2',2''-((1,3,5-triazine-2,4,6-triyl)tris(oxy))tris(N-methoxyacetamide),
3,3',3''-((1,3,5-triazine-2,4,6-triyl)tris(oxy))tris(N-methoxypropanamide),
4,4',4''-((1,3,5-triazine-2,4,6-triyl)tris(oxy))tris(N-methoxybutaneamide),
5,5',5''-((1,3,5-triazine-2,4,6-triyl)tris(oxy))tris(N-methoxypentaneamide),
6,6',6''-((1,3,5-triazine-2,4,6-triyl)tris(oxy))tris(N-methoxyhexaneamide),
2,2'-(pyrimidine-2,4-diylbis(oxy))bis(N-methoxy acetamide),
3,3'-(pyrimidine-2,4-diylbis(oxy))bis(N-methoxy propaneamide),
4,4'-(pyrimidine-2,4-diylbis(oxy))bis(N-methoxy butaneamide),
5,5'-(pyrimidine-2,4-diylbis(oxy))bis(N-methoxy pentaneamide),
6,6'-(pyrimidine-2,4-diylbis(oxy))bis(N-methoxy hexaneamide),
2,2'-(pyrimidine-4,6-diylbis(oxy))bis(N-methoxy acetamide),
3,3'-(pyrimidine-4,6-diylbis(oxy))bis(N-methoxy propaneamide),
4,4'-(pyrimidine-4,6-diylbis(oxy))bis(N-methoxy butaneamide),
5,5'-(pyrimidine-4,6-diylbis(oxy))bis(N-methoxy pentaneamide),
6,6'-(pyrimidine-4,6-diylbis(oxy))bis(N-methoxy hexaneamide),
2,2'-(pyridine-2,3-diylbis(oxy))bis(N-methoxyacetamide),
3,3'-(pyridine-2,3-diylbis(oxy))bis(N-methoxy propaneamide), 4,4'-(pyridine-2,3-diylbis(oxy))bis(N-methoxy butaneamide),
5,5'-(pyridine-2,3-diylbis(oxy))bis(N-methoxy pentaneamide),
6,6'-(pyridine-2,3-diylbis(oxy))bis(N-methoxy hexaneamide),
2,2'-(pyridine-2,4-diylbis(oxy))bis(N-methoxyacetamide),
3,3'-(pyridine-2,4-diylbis(oxy))bis(N-methoxy propaneamide),
4,4'-(pyridine-2,4-diylbis(oxy))bis(N-methoxy butaneamide),
5,5'-(pyridine-2,4-diylbis(oxy))bis(N-methoxy pentaneamide),
6,6'-(pyridine-2,4-diylbis(oxy))bis(N-methoxy hexaneamide),
2,2'-(pyridine-2,5-diylbis(oxy))bis(N-methoxyacetamide),
3,3'-(pyridine-2,5-diylbis(oxy))bis(N-methoxy propaneamide),
4,4'-(pyridine-2,5-diylbis(oxy))bis(N-methoxy butaneamide),
5,5'-(pyridine-2,5-diylbis(oxy))bis(N-methoxy pentaneamide),
6,6'-(pyridine-2,5-diylbis(oxy))bis(N-methoxy hexaneamide),
2,2'-(pyridine-2,6-diylbis(oxy))bis(N-methoxyacetamide),
3,3'-(pyridine-2,6-diylbis(oxy))bis(N-methoxy propaneamide),
4,4'-(pyridine-2,6-diylbis(oxy))bis(N-methoxy butaneamide),
5,5'-(pyridine-2,6-diylbis(oxy))bis(N-methoxy pentaneamide), and
6,6'-(pyridine-2,6-diylbis(oxy))bis(N-methoxy hexaneamide).

In view of ease of synthesis, preferred are sulfur-containing compounds, such as 2,4,6-tris(((vinyloxy)ethyl)thio)-1,3,5-triazine, 2,4,6-tris(((2-vinyloxy)ethyl)thio)pyrimidine and 4,6-bis((2-(vinyloxy)ethyl)thio)pyrimidine. More preferred are 2,4,6-tris(((vinyloxy)ethyl)thio)-1,3,5-triazine and 2,4,6-tris(((2-vinyloxy)ethyl)thio)pyrimidine, and particularly preferred is 2,4,6-tris(((vinyloxy)ethyl)-thio)-1,3,5-triazine.

The compound represented by the formula (1) can be produced in any known manner. For example, it can be obtained by reacting
a compound represented by the following formula (2):

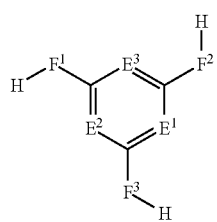

(2)

wherein each of $E^1$ to $E^3$ is independently selected from the group consisting of carbon and nitrogen atoms, provided that at least one of them is a nitrogen atom; and each of $F^1$ to $F^3$ is independently selected from the group consisting of oxygen and sulfur atoms
and
a compound represented by the following formula (3):

(3)

wherein X is selected from the group consisting of chlorine, bromine and iodine atoms; G is a vinyloxy group or a N-methoxymethylamide group; and p is an integer of 0 or more, preferably 2 to 10, more preferably 4 to 10
with a basic compound.

Examples of the nitrogen-containing aromatic compound represented by the formula (2) include: 1,3,5-triazine-2,4,6-trithiol, pyrimidine-2,4,6-trithiol, pyrimidine-4,6-dithiol, pyrimidine-2,4-dithiol, pyridine-2,3-dithiol, pyridine-2,4-dithiol, pyridine-2,5-dithiol, pyridine-2,6-dithiol, 1,3,5-triazine-2,4,6-triol, pyrimidine-2,4,6-triol, pyrimidine-4,6-diol, pyrimidine-2,4-diol, pyridine-2,3-diol, pyridine-2,4-diol, pyridine-2,5-diol and pyridine-2,6-diol. In view of reactivity, preferred are 1,3,5-triazine-2,4,6-trithiol, pyrimidine-2,4,6-trithiol, pyrimidine-4,6-dithiol and pyrimidine-2,4-dithiol, and particularly preferred is 1,3,5-triazine-2,4,6-trithiol. There is no particular restriction on how to obtain the compound of the formula (2), and commercially available compounds are usable. It is possible to use a combination of two or more kinds of the compounds represented by the formula (2).

Examples of the compound represented by the formula (3) include:
chlorine-containing compounds, such as, 1-chloro-3-vinyloxypropane, 1-chloro-4-vinyloxybutane, 1-chloro-5-vinyloxypentane, 1-chloro-6-vinyloxyhexane, 1-chloro-7-vinyloxyheptane, 2-chloro-N-methoxyacetamide, 3-chloro-N-methoxypropanamide, 4-chloro-N-methoxybutaneamide, 5-chloro-N-methoxypentaneamide, and 6-chloro-N-methoxyhexaneamide;
bromine-containing compounds, such as, 1-bromo-3-vinyloxypropane, 1-bromo-4-vinyloxybutane, 1-bromo-5-vinyloxypentane, 1-bromo-6-vinyloxyhexane, 1-bromo-7-vinyloxyheptane, 2-bromo-N-methoxyacetamide, 3-bromo-N-methoxypropanamide, 4-bromo-N-methoxybutaneamide, 5-bromo-N-methoxypentaneamide, and 6-bromo-N-methoxyhexaneamide; and
iodine-containing compounds, such as, 1-iodo-3-vinyloxypropane 1-iodo-4-vinyloxybutane, 1-iodo-5-vinyloxypentane, 1-iodo-6-vinyloxyhexane, 1-iodo-7-vinyloxyheptane, 2-iode-N-methoxyacetamide, 3-iode-N-methoxypropanamide, 4-iode-N-methoxybutaneamide, 5-iode-N-methoxypentaneamide, and 6-iode-N-methoxyhexaneamide. In view of availability, preferred are chlorine-containing compounds, such as, 1-chloro-3-vinyloxypropane, 1-chloro-4-vinyloxybutane, 1-chloro-5-vinyloxypentane, 1-chloro-6-vinyloxyhexane, and 1-chloro-7-vinyloxyheptane. Particularly preferred is 2-chloroethoxyethene. There is no particular restriction on how to obtain the compound of the formula (3), and commercially available compounds are usable.

Two or more kinds of the compounds represented by the formula (3) can be used in combination. For example, it is possible to use a combination of compounds which are represented by the formula (3) but different in the integer p from each other.

According to necessity, the compound of the formula (3) may be partly replaced with another compound, such as, chloroethane, chloromethoxyethene, 2-chloroethoxyethene, bromothane, bromomethoxy-ethene, 2-bromoethoxyethene, iodothane, iodomethoxy-ethene or 2-iodoethoxyethene. If used, in view of availability, preferred are chlorine-containing compounds, such as, chloromethoxyethene, 2-chloroethoxyethene, 1-chloro-3-vinyloxypropane, 1-chloro-4-vinyloxybutane, 1-chloro-5-vinyloxypentane, 1-chloro-6-vinyloxyhexane, and 1-chloro-7-vinyloxyheptane; and particularly preferred is 2-chloroethoxyethane. There is no particular restriction on how to obtain those compounds, and commercially available compounds are usable.

The compound represented by the formula (3) is used in an amount of 3 to 27 equivalents in total, preferably 6 to 18 equivalents in total, based on the molar amount of the compound represented by the formula (2).

Examples of the basic compound include;
alkali metal hydroxides, such as,
lithium hydroxide, sodium hydroxide, potassium hydroxide, rubidium hydroxide, and cesium hydroxide;
alkali metal oxides, such as,
sodium oxide and potassium oxide;
alkaline earth metal hydroxides, such as,
beryllium hydroxide, magnesium hydroxide, calcium hydroxide, barium hydroxide, and strontium hydroxide;
alkaline earth metal oxides, such as,
beryllium oxide, magnesium oxide, calcium oxide, strontium oxide, and barium oxide;
organic alkali metals, such as,
methyllithium, ethyllithium, n-butyllithium, s-butyllithium, t-butyllithium, phenyllithium, lithium diisopropylamide, and lithium hexamethyldisilazide;
organic alkaline earth metals, such as,
dimethylmagnesium, diethylmagnesium, methylmagnesium chloride, methylmagnesium bromide, ethylmagnesium bromide, and phenylmagnesium bromide;
alkoxy compounds, such as,
sodium methoxide, sodium ethoxide, sodium propoxide, and potassium t-butoxide;
metal hydrides, such as,
sodium hydride, potassium hydride, and calcium hydride;
tetraalkylammonium hydroxides, such as,
tetramethylammonium hydroxide and tetrabutyl-ammonium hydroxide; and
alkali metal carbonates, such as,
lithium carbonate, sodium carbonate, potassium carbonate, and calcium carbonate. In view of reactivity, preferred are alkali metal carbonates, such as, lithium carbonate, sodium carbonate, potassium carbonate and calcium carbonate; and particularly preferred is potassium carbonate. Commercially available potassium carbonate is usable. The basic compound is used in an amount of normally 3 to 27 equivalents, preferably 6 to 18 equivalents, based on the molar amount of the compound represented by the formula (2).

The above components are made to react preferably at a temperature high enough to ensure a sufficient reaction rate but low enough to avoid formation of unfavorable by-products. In consideration of that, the reaction temperature is normally −50 to 150° C., preferably 20 to 100° C.

The reaction may be carried out either without or in the presence of a solvent. However, since the reaction yield can be improved and purification procedures can be easily performed, the reaction is preferably carried out in the presence of a solvent.

In the case where the reaction is carried out in the presence of a solvent, the solvent is not particularly restricted unless it gives adverse effects to the reaction. Preferred examples of the solvent include N,N-dimethylformamide, N,N-dimethylacetamide, dimethyl sulfoxide and N-methylpyrrolidone. Particularly preferred is dimethyl sulfoxide. In view of the reaction rate and the reaction yield, the amount of the solvent is normally 0.5 to 20 times, preferably 1 to 10 times, more preferably 1.5 to 5 times as much as that of the compound represented by the formula (2) by volume.

After the reaction, the aimed product can be isolated and purified from the reaction solution by use of techniques normally used in organic syntheses. For example, after water is added so as to remove the basic compound, the solution is well stirred and then the organic portion is collected and dried with a desiccant such as anhydrous magnesium sulfate. Successively, the solvent is distilled away from the dried organic portion under reduced pressure, to obtain the aimed product. If necessary, the product can be purified by column chromatography.

(Composition for Forming a Bottom Anti-Reflective Coating)

The composition for forming a bottom anti-reflective coating according to the present invention comprises the above cross-linking agent, a polymer having a particular aromatic group, and a solvent. If necessary, the composition further comprises other additives such as a photo acid generator, thermal acid generators, bases, photodecomposable bases, photobase generators and surfactants. Some of these components are individually described below.

Polymer Having an Aromatic Group

The cross-linking agent of the present invention can be incorporated in the composition for forming a bottom anti-reflective coating, and the composition may contain any polymer. However, the cross-linking agent is preferably used in the composition comprising a polymer represented by the following formula (4):

$$-A_m\text{-}B_n\text{-} \quad (4)$$

wherein
A and B are repeating units represented by the following formulas (A) and (B), respectively;

(A)

(B)

in which
each of $R^1$ and $R^2$ is independently a group selected from the group consisting of a hydrogen atom and alkyl groups, and is preferably a hydrogen atom or a methyl group;
L is a linking group selected from the group consisting of a single bond, straight-chain and branched chain alkylene groups having one or more carbon atoms (such as $C_1$ to $C_{12}$), and COO; and is preferably COO;
Y is an aromatic group containing one or more benzene rings, provided that the aromatic group may or may not have a substituent selected from the group consisting of alkyl, aryl, halogen atoms, alkoxy, nitro, aldehyde, cyano, amide, dialkylamino, sulfonamide, imide, carboxy, carboxylic acid ester, sulfo, sulfonic acid ester, alkylamino, and arylamino, and also provided that one of the benzene rings contained in the aromatic group may be replaced with a quinone ring; and Z is a group selected from the group consisting of $R^3COOR^4$ and $R^3OR^4$, in which $R^3$ is a linking group selected from the group consisting of single bond, oxygen atom, aromatic ring, and straight-chain and branched chain alkylene groups which have one or more, preferably 1 to 6 carbon atoms and which may be substituted with a fluorine atom, and also in which $R^4$ is a group selected from the group consisting of a hydrogen atom, substituted hydrocarbon groups and non-substituted hydrocarbon groups;

the repeating units A and B may be connected either randomly or to form a block, each of the repeating units A and B may be a combination of two or more repeating units having different structures, and m and n are numbers indicating polymerization degrees, and are a number of 10 or more and a number of 0 or more, respectively.

The above polymer can be produced by polymerizing monomers corresponding to the repeating units (A) and (B) in the formula (4).

The polymer of the formula (4) has the group Y, which is an aromatic group containing one or more benzene rings. The group Y enhances absorption of light at a particular wavelength and thereby gives an optical effect of the resultant bottom anti-reflective coating. There is no upper limit on the number of benzene rings contained in the aromatic group, but the number of benzene rings is preferably 5 or less. The aromatic group may contain five-membered and seven-membered hydrocarbon rings, but they are preferably not present.

Examples of the aromatic group contained in the group Y include: benzene, naphthalene, anthracene, phenanthrene, tetracene, chrysene, benzo[c]-phenanthrene, triphenylene, pentacene, picene, and benzo[c]chrysene. Those aromatic groups may have substituents selected from the group consisting of alkyl, aryl, halogen atoms, alkoxy, nitro, aldehyde, cyano, amide, dialkylamino, sulfonamide, imide, carboxy, carboxylic acid ester, sulfo, sulfonic acid ester, alkylamino, and arylamino. One of the benzene rings contained in the above aromatic groups may be replaced with a quinone ring. Examples thereof include: anthraquinone, 5,12-naphthacenequinone (tetracenequinone), 5,6-chrysenequinone, 5,12-chrysenequinone, and 6,13-pentacenequinine.

Since the group Y greatly contributes to light absorption of the polymer, it is preferably selected according to wavelength of the light employed for exposure. For example, if the exposure light source is a KrF laser, the group Y preferably contains anthracene or the like, which has high absorption of light at the wavelength of the KrF laser beam (wavelength: 248 nm).

Examples of the monomer corresponding to the repeating unit (A) include: 9-anthracenemethyl acrylate, 9-tetracenemethyl acrylate, 9-pentacenemethyl acrylate, 9-anthracenemethyl methacrylate, 9-tetracenemethyl methacrylate, and 9-pentacenemethyl methacrylate. In view of availability, preferred is 9-anthracenemethyl methacrylate. It is possible to use in combination two or more kinds of the monomers corresponding to the repeating unit (A). There is no particular restriction on how to obtain the monomer, and commercially available monomers may be used or otherwise they may be synthesized to use. The monomer is used in an amount of preferably 10 to 40 mol %, more preferably 20 to 30 mol %, provided that the total amount of all the monomers constituting the polymer of the formula (4) is regarded as 100 mol %.

On the other hand, in the polymer of the formula (4), the repeating unit (B) serves as a part reactable with the cross-linking agent represented by the formula (1). In the composition cast on the substrate, the cross-linking agent reacts with the part of the repeating unit (B) to form a cross-linking structure in the polymer.

Examples of the monomer corresponding to the repeating unit (B) include: acrylic acid, 3-butenoic acid, 4-pentenoic acid, 5-hexenoic acid, 6-heptenoic acid, 7-octenoic acid, 8-nonenoic acid, methacrylic acid, 2-methyl-3-butenoic acid, 2-methyl-4-pentenoic acid, 2-methyl-5-hexenoic acid, 2-methyl-6-heptenoic acid, 2-methyl-7-octenoic acid, 2-methyl-8-nonenoic acid, 4-vinylbenzoic acid, tert-butyl benzoate, tert-butyl methacrylate, 9-hydroxynaphthyl methacrylate, 9-hydroxynaphthyl acrylate, 4-hydroxyphenyl methacrylate, 4-hydroxyphenyl acrylate, and 4-hydroxystyrene. In view of availability, preferred are acrylic acid, methacrylic acid, 4-hydroxyphenyl methacrylate and 4-hydroxystyrene. There is no particular restriction on how to obtain the monomer, and commercially available monomers can be used or otherwise they may be synthesized to use. It is possible to use in combination two or more kinds of the monomers corresponding to the repeating unit (B). For example, as the monomer corresponding to the repeating unit (B), methacrylic acid or 4-hydroxystyrene can be used in combination with acrylic acid or 4-hydroxystyrene. The monomer is used in an amount of preferably 60 to 90 mol %, more preferably 70 to 80 mol %, provided that the total amount of all the monomers constituting the polymer of the formula (4) is regarded as 100 mol %.

The polymerization for forming the polymer of the formula (4) can be carried out in a proper solvent by use of the above monomers as the starting materials with a radical or ionic polymerization initiator. The polymer of the formula (4) can have any structure such as random copolymer or block copolymer, and hence the polymerization conditions are selected according to the aimed structure.

Examples of the polymerization initiator include 2,2'-azobis(isobutyronitrile) (AIBN), 2,2'-azobis-dimethyl-(2-methylpropionate), 2,2'-azobis-(4-methoxy-2,4-dimethylvaleronitrile), 2,2'-azobis-(2-cyclopropylpropionitrile), 2,2'-azobis(2,4-dimethylvaleronitrile), 2,2'-azobis(2,4-dimethylpentane-nitrile), 1,1'-azobis(cyclohexanecarbonitrile), benzoyl peroxide, t-butyl peroxide benzoate, di-t-butyldiperoxy phthalate, t-butylperoxy-2-ethylhexanoate, t-butylperoxy pivalate, t-amylperoxypivalate, and butyllithium. In view of safety and availability, preferred are 2,2'-azobis(isobutyronitrile) (hereinafter, often referred to as "AIBN") and 2,2'-azobis-dimethyl-(2-methylpropionate). The amount thereof is preferably 1 to 10 wt % based on the total weight of all the monomers.

Examples of the solvents preferably used for the polymerization reaction include: toluene, tetrahydrofuran, benzene, methyl amyl ketone, dimethylformamide, dimethyl sulfoxide, ethyl lactate, and propyleneglycol monomethyl ether acetate (PGMEA). Those solvents may be used singly or in combination of two or more. The amount thereof is preferably 1 to 10 times as large as the total weight of all the monomers.

The polymerization reaction is conducted at a temperature of normally 50 to 200° C., preferably 60 to 150° C., more preferably 80 to 120° C.

In the present invention, there is no particular restriction on the molecular weight of the polymer represented by the formula (4). However, when measured in terms of standard polystyrene by gel permeation chromatography (GPC), the weight average molecular weight thereof is preferably in the range of 2000 to 5000000 Da. Further, in consideration of film formability, solubility and heat stability, it is more preferred for the polymer of the formula (4) to have a weight average molecular weight of 3000 to 100000 Da. The molecular weight of the polymer, which is obtained by the polymerization reaction, can be controlled by various polymerization conditions such as polymerization time and temperature, concentrations of the monomers and the initiator used in the reaction, and the reaction solvent. If ionic polymerization is selected as the polymerization reaction, the polymer having a narrow molecular weight distribution can be obtained.

After the polymerization reaction is completed, the polymer can be separated and purified from the reaction solution by use of techniques adopted in normal polymer syntheses. For example, n-hexane or n-heptane, which is a poor solvent of the polymer but a good solvent of the polymerization solvent, is poured into the reaction solution so as to separate the polymer. However, without separating or purifying the polymer, the mixture solution obtained by the polymerization reaction may be directly used as a material of the composition for forming a bottom anti-reflective coating.

As long as all the components are homogeneously dissolved in the composition of the present invention for forming a bottom anti-reflective coating, there is no particular restriction on the concentration of the polymer represented by the formula (4). However, in view of controlling the thickness, the concentration thereof is preferably 1 to 10 wt %, more preferably 1 to 2 wt % based on the total weight of the composition.

(Solvent)

Any solvent can be used in the composition of the present invention for forming a bottom anti-reflective coating, as long as it can dissolve all the components. Examples of the solvent include ethyleneglycol monomethyl ether, ethyleneglycol monoethyl ether, methyl cellosolve acetate, ethyl cellosolve acetate, diethyleneglycol monomethyl ether, diethyleneglycol monoethyl ether, propylene glycol, propyleneglycol monomethyl ether, propyleneglycol monomethyl ether acetate, propyleneglycol propyl ether acetate, toluene, xylene, methyl ethyl ketone, cyclopentanone, cyclohexanone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxypropionate, ethyl 3-methoxypropionate, ethyl 3-ethoxypropionate, methyl 3-ethoxypropionate, methyl pyruvate, ethyl pyruvate, ethyl acetate, butyl acetate, ethyl lactate, butyl lactate, N,N-dimethylformamide, N,N-dimethylacetamide, and N-methylpyrrolidone. Those solvents can be used singly or in combination of two or more. Further, they may be used in combination with high boiling point solvents such as propyleneglycol monobutyl ether and propyleneglycol monobutyl ether acetate.

(Photo Acid Generator)

According to necessity, the composition of the present invention for forming a bottom anti-reflective coating contains a photo acid generator. In order to assist the cross-linked polymer in decross-linking when subjected to exposure and thereby to make the aimed bottom anti-reflective coating both developable and photo-sensitive, the composition preferably contains a photo acid generator. As the photo acid generator, any compound can be used as long as it generates acid when exposed to light of KrF excimer laser (wavelength: 248 nm), ArF excimer laser (wavelength: 193 nm) or the like.

The photo acid generator can be freely selected from conventionally known ones. Examples of the photo acid generator include onium salt compounds, cross-linkable onium salt compounds, sulfone maleimide derivatives, and disulfonyl diazomethane compounds.

Examples of the onium salt compounds include but not limited to: iodonium salt compounds, such as, diphenyliodonium hexafluorophosphate, diphenyliodonium trifluoromethanesulfonate, diphenyliodonium nonafluoro-n-butanesulfonate, diphenyliodonium per-fluoro-n-octanesulfonate, diphenyliodonium camphor-sulfonate, bis(4-tert-butylphenyl)iodonium camphor-sulfonate, and bis(4-tert-butylphenyl)iodonium trifluoromethanesulfonate; sulfonium salt compounds, such as triphenylsulfonium hexafluoroantimonate, triphenylsulfonium nona-fluoro-n-butanesulfonate, triphenylsulfonium camphor-sulfonate, and triphenylsulfonium trifluoromethanesulfonate; and cross-linkable onium salt compounds, such as, bis(4-hydroxyphenyl)(phenyl)sulfonium trifluoromethanesulfonate, bis(4-hydroxyphenyl)(phenyl)-sulfonium 1,1,2,2,3,3,4,4,4-nonafluoro-butane-1-sulfonate, phenylbis(4-(2-(vinyloxy)ethoxy)-phenyl)sulfonium 1,1,2,2,3,3,4,4-octafluoro-butane-1,4-disulfonate, and tris(4-(2-(vinyloxy)ethoxy)-phenyl)sulfonium 1,1,2,2,3,3,4,4-octafluoro-butane-1,4-disulfonate.

Examples of the sulfone maleimide derivatives include N-(trifluoromethanesulfonyloxy)succinimide, N-(fluoro-n-butanesulfonyloxy)succinimide, N-(camphor-sulfonyloxy)succinimide, and N-(trifluoromethane-sulfonyloxy)naphthalimide.

Examples of the disulfonyl diazomethane compounds include bis(trifluoromethylsulfonyl)diazomethane, bis(cyclohexylsulfonyl)diazomethane, bis(phenylsulfonyl)diazomethane, bis(p-toluenesulfonyl)-diazomethane, bis(2,4-dimethylbenzenesulfonyl)diazomethane, and methylsulfonyl-p-toluenesulfonyldiazomethane. The composition of the present invention for forming a bottom anti-reflective coating can contain those photo acid generators in combination of two or more.

Other Components

The composition according to the present invention for forming a bottom anti-reflective coating can contain other supplementary components according to necessity. Examples of the supplementary components include polymers other than the polymer of the formula (4), surfactants, and smoothing agents. They should not degrade the effect of the present invention.

Composition for Forming a Bottom Anti-Reflective Coating

The composition of the present invention for forming a bottom anti-reflective coating can be prepared by mixing and dissolving the above components homogeneously. There is no particular restriction on the amounts of the components, and they are properly determined according to the aimed coating.

For example, the composition of the present invention contains the cross-linking agent of the formula (1) in an amount of preferably 5 to 40 weight parts, more preferably 10 to 30 weight parts based on 100 weight parts of the polymer represented by the formula (4).

The amount of the polymer represented by the formula (4) is preferably 1 to 10 wt %, more preferably 1 to 3 wt % based on the total weight of the composition.

The amount of the photo acid generator is preferably 0.01 to 20 weight parts, more preferably 0.02 to 5 weight parts based on 100 weight parts of the polymer of the formula (4). The photo acid generator has a function of enabling to regulate the form of the photoresist. The reason of that is not fully revealed, but it is presumed that the photo acid generator controls the acidity of the bottom anti-reflective coating. Consequently, addition of the photo acid generator makes it possible to form a favorable rectangular photoresist pattern.

The composition obtained by mixing the components is preferably used after filtrated through a 0.2 to 0.05 μm porous size filter. The composition thus prepared is excellent in storage stability at room temperature for a long time.

(Process for Forming a Bottom Anti-Reflective Coating and Pattern Formation Method)

The following describes a process for forming a bottom anti-reflective coating of the present invention and a pattern formation method of the present invention.

The composition of the present invention for forming a bottom anti-reflective coating is cast by proper means, such as a spinner or a coater, on a semiconductor substrate (e.g., silicon/silicon dioxide-coated substrate, silicon nitride substrate, silicon wafer substrate, glass substrate, ITO substrate). The composition contains, at least, a cross-linking agent represented by the formula (1), a polymer represented by the formula (4), and a solvent. The composition cast on the substrate is then fired to form a bottom anti-reflective coating. The baking conditions are properly determined. For example, the baking temperature is generally 80 to 250° C., preferably 100 to 250° C.; and the baking time is generally 0.3 to 5 minutes, preferably 0.5 to 2 minutes. In this baking procedure, a hardening reaction proceeds in the cast composition to form a bottom anti-reflective coating.

On the bottom anti-reflective coating thus formed, for example, a positive-working photoresist composition is applied. Here, the "positive-working photoresist" means a substance that causes a reaction under exposure to light and thereby increases solubility in an alkaline developing solution. There is no particular restriction on the photoresist, and any positive-working photoresist, negative-working photoresist or negative tone development (NTD) photoresist can be adopted as long as it is sensitive to light of exposure for pattern formation.

Thereafter, the exposure is carried out by use of a predetermined mask. There is no particular restriction on the wavelength of light used for exposure, but it is preferred to use light of 13.5 to 248 nm. Examples of the light include KrF excimer laser light (wavelength: 248 nm), ArF excimer laser light (wavelength: 193 nm) and extreme UV light (wavelength: 13.5 nm). If the exposure is performed by use of light of very short wavelength, such as extreme UV light, the light intensity is generally so weak that the bottom anti-reflective coating is not very effective in preventing light-reflection, but the coating functions to inhibit adverse effects of gases given off from the substrate placed thereunder. After the exposure, post-exposure bake can be carried out. The temperature of post-exposure bake is 80 to 150° C., preferably 100 to 140° C.; and the time thereof is 0.3 to 5 minutes, preferably 0.5 to 2 minutes.

Successively, the development is carried out by use of a developing solution. Thereby, in the area exposed to light, the positive-working photoresist layer and the bottom anti-reflective coating placed thereunder are developed and removed to form a photoresist pattern.

The developing solution used in the above pattern formation method is, for example, an alkaline aqueous solution. Examples of the alkaline developing solution include: an aqueous solution of alkali metal hydroxide, such as potassium hydroxide or sodium hydroxide; an aqueous solution of tertiary ammonium hydroxide, such as tetramethylammonium hydroxide, tetraethylammonium hydroxide or choline; and an aqueous solution of amine, such as ethanolamine, propylamine or ethylenediamine. Particularly preferred is a 2.38 wt % TMAH aqueous solution, which is commonly used as an alkaline developing solution. Those developing solutions enable to dissolve and remove the bottom anti-reflective coating readily at room temperature. The developing solutions may contain surfactants and the like.

The temperature of the developing solution is generally 5 to 50° C., preferably 25 to 40° C.; and the developing time is generally 10 to 300 seconds, preferably 30 to 60 seconds.

The present invention is further explained by use of the following examples, but they by no means restrict embodiments of the present invention. In the description of the examples, "parts" and "%" mean "weight parts" and "wt %", respectively, unless otherwise noted.

Example 1

Synthesis of 2,4,6-tris(((vinyloxy)ethyl)-thio)-1,3,5-triazine (Cross-Linking Agent C1)

Calcium carbonate (7464 parts), dimethyl sulfoxide (7876 parts) and 2-chloroethoxyethene (5872 parts) were placed in a reaction vessel equipped with a stirrer, a condenser, a heater and a thermostat; and then heated to 90° C.

Independently, 1,3,5-triazine-2,4,6-trithiol (1097 parts) and dimethyl sulfoxide (8355 parts) were placed in another vessel, and stirred. The obtained solution was dropped into the above reaction vessel from a dropping funnel, and then the mixture was kept at 90° C. for 8 hours.

After the mixture solution was cooled to room temperature, 5% sodium hydroxide aqueous solution (10000 parts) and diethyl ether (10000 parts) were added therein. The diethyl ether portion was collected, and then a saturated aqueous solution of sodium hydrogen carbonate (10000 parts) was added therein. After the organic portion was collected, water (10000 parts) was added therein. The organic portion was again collected, and then diethyl ether and 2-chloroethoxyethene were distilled away from the organic portion at room temperature under reduced pressure. Thus, 2,4,6-tris(((vinyloxy)ethyl)thio)-1,3,5-triazine (cross-linking agent C1) was obtained in the yield of 90%.

(Spectral Data of the Cross-Linking Agent C1)
$^1$H-NMR (CDCl$_3$, δ in ppm): 6.46 (dd, 3H, J=7.0 and 3.4 Hz, C$\underline{H}$=CH$_2$), 4.23 (dd, 3H, J=7.2 and 1.0 Hz, CH=C$\underline{H}_2$), 4.06 (dd, 3H, J=3.4 and 1.2 Hz, CH=C$\underline{H}_2$), 3.94 (t, 6H, J=6.4, C$\underline{H}_2$O), 3.37 (t, 6H, J=6,6, SC$\underline{H}_2$),
$^{13}$C-NMR (CDCl$_3$): 179.09, 151.25, 87.27, 65.89, 29.05

Example 2

Synthesis of 2,4,6-tris(2-vinyloxy)ethoxy)-1,3,5-triazine (Cross-Linking Agent C2)

Calcium carbonate (7464 parts), dimethyl sulfoxide (7876 parts) and 2-chloroethoxyethene (5872 parts) were placed in a reaction vessel equipped with a stirrer, a condenser, a heater and a thermostat; and then heated to 90° C.

Independently, 1,3,5-triazine-2,4,6-triol (1097 parts) and dimethyl sulfoxide (8355 parts) were placed in another vessel, and stirred. The obtained solution was dropped into the above reaction vessel from a dropping funnel, and then the mixture was kept at 90° C. for 8 hours.

After the mixture solution was cooled to room temperature, 5% sodium hydroxide aqueous solution (10000 parts) and diethyl ether (10000 parts) were added therein. The diethyl ether portion was collected, and then a saturated aqueous solution of sodium hydrogen carbonate (10000 parts) was added therein. After the organic portion was collected, water (10000 parts) was added therein. The organic portion was again collected, and then diethyl ether and 2-chloroethoxyethene were distilled away from the organic portion at room temperature under reduced pressure. Thus, 2,4,6-tris(2-vinyloxy)ethoxy)-1,3,5-triazine (cross-linking agent C2) was obtained in the yield of 70%.
(Spectral Data of the Cross-Linking Agent C2)
$^1$H-NMR (CDCl$_3$, δ in ppm): 6.45 (dd, 3H, J=7.0 and 3.4 Hz, CH═CH$_2$), 4.51 (t, 6H, J=6.6 Hz, CH$_2$CH$_2$OCH), 4.33 (t, 6H, J=6.6 Hz, CH$_2$CH$_2$OCH), 4.15 (dd, 3H, J=7.2 and 1.0 Hz, CH═CH$_2$), 4.03 (dd, 3H, J=3.4 and 1.2 Hz, CH═CH$_2$),
$^{13}$C-NMR (CDCl$_3$): 172.70, 151.80, 84.60, 69.4, 67.5

Example 3

Synthesis of 4,6-bis(2-(vinyloxy)ethoxy)pyrimidine (Cross-Linking Agent C3)

Calcium carbonate (7464 parts), dimethyl sulfoxide (7876 parts) and 2-chloroethoxyethene (5872 parts) were placed in a reaction vessel equipped with a stirrer, a condenser, a heater and a thermostat; and then heated to 90° C.

Independently, pyrimidine-4,6-diol (1097 parts) and dimethyl sulfoxide (8355 parts) were placed in another vessel, and stirred. The obtained solution was dropped into the above reaction vessel from a dropping funnel, and then the mixture was kept at 90° C. for 8 hours.

After the mixture solution was cooled to room temperature, 5% sodium hydroxide aqueous solution (10000 parts) and diethyl ether (10000 parts) were added therein. The diethyl ether portion was collected, and then a saturated aqueous solution of sodium hydrogen carbonate (10000 parts) was added therein. After the organic portion was collected, water (10000 parts) was added therein. The organic portion was again collected, and then diethyl ether and 2-chloroethoxyethene were distilled away from the organic portion at room temperature under reduced pressure. Thus, 4,6-bis(2-(vinyloxy)ethoxy)pyrimidine (cross-linking agent C3) was obtained in the yield of 70%.
(Spectral Data of the Cross-Linking Agent C3)
$^1$H-NMR (CDCl$_3$, δ in ppm): 9.59 (s, 1H), 6.45 (dd, 3H, J=7.0 and 3.4 Hz, CH═CH$_2$), 6.44 (s, 1H), 4.51 (t, 6H, J=6.6 Hz, CH$_2$CH$_2$OCH), 4.33 (t, 6H, J=6.6 Hz, CH$_2$CH$_2$OCH), 4.15 (dd, 3H, J=7.2 and 1.0 Hz, CH═CH$_2$), 4.03 (dd, 3H, J=3.4 and 1.2 Hz, CH═CH$_2$),
$^{13}$C-NMR (CDCl$_3$): 170.5, 161.9, 151.8, 84.6, 82.1, 69.4, 67.5

Example 4

Synthesis of 2,3-bis(2-(vinyloxy)ethoxy)pyridine (Cross-Linking Agent C4)

Calcium carbonate (7500 parts), dimethyl sulfoxide (7900 parts) and 2-chloroethoxyethene (5800 parts) were placed in a reaction vessel equipped with a stirrer, a condenser, a heater and a thermostat; and then heated to 90° C.

Independently, pyridine-2,3-diol (1000 parts) and dimethyl sulfoxide (7900 parts) were placed in another vessel, and stirred. The obtained solution was dropped into the above reaction vessel from a dropping funnel, and then the mixture was kept at 90° C. for 8 hours.

After the mixture solution was cooled to room temperature, 5% sodium hydroxide aqueous solution (10000 parts) and diethyl ether (10000 parts) were added therein. The diethyl ether portion was collected, and then a saturated aqueous solution of sodium hydrogen carbonate (10000 parts) was added therein. After the organic portion was collected, water (10000 parts) was added therein. The organic portion was again collected, and then diethyl ether and 2-chloroethoxyethene were distilled away from the organic portion at room temperature under reduced pressure. Thus, 2,3-bis(2-(vinyloxy)ethoxy)pyridine (cross-linking agent C4) was obtained in the yield of 78%.
(Spectral Data of the Cross-Linking Agent C4)
$^1$H-NMR (CDCl$_3$, δ in ppm): 8.06 (d, 1H, J=4.4 Hz. CHN), 7.30 (d, 1H, J=4.4 Hz. CHCS), 6.78 (m, 1H), 6.45 (dd, 2H, J=7.0 and 3.4 Hz, CH═CH$_2$), 4.15 (dd, 2H, J=7.2 and 1.0 Hz, CH═CH$_2$), 4.03 (dd, 2H, J=3.4 and 1.2 Hz, CH═CH$_2$), 3.94 (t, 4H, J=6.4 Hz, CH$_2$O), 3.61 (t, 4H, J=6.6 Hz, SCH$_2$),
$^{13}$C-NMR (CDCl$_3$): 151.8, 146.3, 146.1, 145.5, 132.2, 125.2, 84.6, 66.8, 39.8

Example 5

Synthesis of 2,4,6-tris((4-vinyloxy)butyl)-thio)-1,3,5-triazine (Cross-Linking Agent C5)

Calcium carbonate (7400 parts), dimethyl sulfoxide (7800 parts) and 1-chloro-4-(vinyloxy)butane (5800 parts) were placed in a reaction vessel equipped with a stirrer, a condenser, a heater and a thermostat; and then heated to 90° C.

Independently, 2,4,6-tris(((vinyloxy)ethyl)-thio)-1,3,5-triazine (1000 parts) and dimethyl sulfoxide (8300 parts) were placed in another vessel, and stirred. The obtained solution was dropped into the above reaction vessel from a dropping funnel, and then the mixture was kept at 90° C. for 8 hours.

After the mixture solution was cooled to room temperature, 5% sodium hydroxide aqueous solution (10000 parts) and diethyl ether (10000 parts) were added therein. The diethyl ether portion was collected, and then a saturated aqueous solution of sodium hydrogen carbonate (10000 parts) was added therein. After the organic portion was collected, water (10000 parts) was added therein. The organic portion was again collected, and then diethyl ether and 2-chloroethoxyethene were distilled away from the organic portion at room temperature under reduced pressure. Thus, 2,4,6-tris((4-vinyloxy)butyl)thio)-1,3,5-triazine (cross-linking agent C5) was obtained in the yield of 88%.
(Spectral Data of the Cross-Linking Agent C5)
$^1$H-NMR (CDCl$_3$, δ in ppm): 6.45 (dd, 3H, J=7.0 and 3.4 Hz, CH═CH$_2$), 4.15 (dd, 3H, J=7.2 and 1.0 Hz, CH═CH$_2$), 4.03 (dd, 3H, J=3.4 and 1.2 Hz, CH═CH$_2$), 4.01 (t, 6H, J=6.4 Hz, CH$_2$O), 3.10 (t, 6H, J=6.6 Hz, SCH$_2$), 1.71 (m, 6H, OCH$_2$CH$_2$), 1.66 (m, 6H, SCH$_2$CH$_2$),
$^{13}$C-NMR (CDCl$_3$): 181.1, 151.1, 81.3, 66.5, 36.7, 29.0, 26.6

Polymer Synthesis Example 1

Synthesis of HS/AMMA/MAA (50/25/25) Terpolymer (Polymer P1)

Propyleneglycol monomethyl ether acetate (2000 parts) as a solvent was placed in a reaction vessel equipped with a stirrer, a condenser, a heater and a thermostat. The solvent was purged with nitrogen gas for 30 minutes, and then heated to 90° C.

Independently, 9-anthracene-methyl methacrylate (AMMA, 1582 parts), acetoxy styrene (1857 parts), methacrylic acid (MAA, 493 parts), azobis(isobutyronitrile) (radical polymerization initiator AIBN, 118 parts), and propyleneglycol monomethyl ether acetate (7450 parts) were placed in another vessel, and stirred. The obtained monomer solution was purged with nitrogen gas for 30 minutes.

The monomer solution was then introduced into the reaction vessel over a period of 2 hours by means of a peristaltic pump. After the introduction was completed, the reaction mixture was kept at 90° C. for 4 hours.

After cooled to room temperature, the mixture was poured into n-heptane (50000 parts). The top clear portion was then removed, and the left reaction mixture was dissolved in tetrahydrofuran (7000 parts). The obtained solution was poured into n-heptane (50000 parts) to form white precipitates. The precipitates were isolated by filtration under reduced pressure, and dried overnight in a vacuum oven at 50° C.

After drying, tetrahydrofuran (7000 parts), 25% TMAH methanol solution (3090 parts) and water (10000 parts) were added and then the mixture was stirred at room temperature for 2 hours. After the reaction was completed, 0.5% HCl (64000 parts) was added into the reaction solution to form white precipitates. The precipitates were isolated by filtration under reduced pressure, and then dissolved in tetrahydrofuran (7000 parts). The obtained solution was poured into water (50000 parts) to form white precipitates. The precipitates were isolated by filtration under reduced pressure, and dried overnight in a vacuum oven at 50° C.

As a result of drying, HS/AMMA/MAA (50/25/25) terpolymer (Polymer P1) was obtained in the form of white powder (yield: 75%). The molecular weight of the product was measured by means of GPC (THF), to find that the product had a weight average molecular weight Mw of 8903 Da, a number average molecular weight Mn of 4287 Da and a polydispersity index PDI of 2.08.

Polymer Synthesis Example 2

Synthesis of PQMA/AMMA/EtCpMA (66/22.5/11.5) Terpolymer (Polymer P2)

In a 250 mL round-bottom flask equipped with a mechanical stirrer, a condenser, a nitrogen gas inlet and a thermostat, 384 g of propyleneglycol monomethyl ether acetate (PGMEA) solvent, 6.24 g of 2-ethylcyclopentyl methacrylate (EtCpMA), 34.99 g of 4-hydroxyphenyl methacrylate (PQMA), 18.50 g of 9-anthracenemethyl methacrylate (AMMA) and 5.97 g of azobis(isobutyronitrile) (AIBN) initiator were mixed and purged with nitrogen gas for 30 minutes. The deaerated reaction mixture was heated by means of a heating mantle at 70° C. for 5 hours, to promote the polymerization. Thereafter, the reaction mixture was cooled to room temperature under nitrogen atmosphere. When the temperature of the mixture reached down to 30° C., 9 g of methanol was added so as to terminate the reaction. The obtained PGMEA solution was poured into twice volumes of hexane, to precipitate the polymer. The precipitated polymer was collected and washed three times with a mixture of water and methanol, and then dried at 40° C. for 48 hours.

As a result of the above procedure, 56.66 g of Polymer P2 was obtained (yield: 94.9%). The molecular weight of the product was measured, to find that the product had a weight average molecular weight Mw of 21910 Da, a number average molecular weight Mn of 8572 Da and a polydispersity index PDI of 2.56, Polymer Synthesis Example 3

Synthesis of PQMA/AMMA/EdMA/MAA (54/29/12/5) Tetrapolymer (Polymer P3)

In a 250 mL round-bottom flask equipped with a mechanical stirrer, a condenser, a nitrogen gas inlet and a thermostat, 31 g of methyl amyl ketone (MAK) was placed and purged with nitrogen gas for 30 minutes. The deaerorated solvent was then heated at 80° C. Independently, 3.95 g of 2-ethyladamantyl methacrylate (EAdMA), 12.98 g of 4-hydroxyphenyl methacrylate (PQMA), 10.25 g of 9-anthracenemethyl methacrylate (AMMA), 0.57 g of methacrylic acid (MAA) and 1.11 g of azobis(isobutyronitrile) (AIBN) initiator were dissolved in 70 g of MAK, and then purged with nitrogen gas for 30 minutes. The obtained deaerated mixture was added over a period of 3 hours into the above pre-heated solvent in the flask by means of a syringe pump. The reaction mixture was further kept heated at 80° C. for 3 hours, to promote the polymerization. Thereafter, the reaction mixture was cooled to room temperature under nitrogen atmosphere. When the temperature of the mixture reached down to 30° C., 4 g of methanol was added so as to terminate the reaction. The obtained MAK solution was poured into twice volumes of hexane, to precipitate the polymer. The precipitated polymer was collected and washed three times with a mixture of water and methanol, and then dried at 40° C. for 48 hours.

As a result of the above procedure, 26.90 g of Polymer P3 was obtained (yield: 93.2%). The molecular weight of the product was measured, to find that the product had a weight average molecular weight Mw of 10701 Da, a number average molecular weight Mn of 5515 Da and a polydispersity index PDI of 1.94.

Polymer Synthesis Example 4

Synthesis of AMMA/MAA (20/80) Copolymer (Polymer P4)

In a reaction vessel equipped with a stirrer, a condenser, a heater and a thermostat, N,N'-dimethylformamide (150 parts) and methyl amyl ketone (150 parts) were placed to prepare a mixed solvent. The solvent was purged with nitrogen gas for 30 minutes, and then heated to 120° C.

Independently, 9-anthracene-methyl methacrylate (AMMA, 279 parts), methacrylic acid (MAA, 534 parts), dimethyl 2,2'-azobis(2-methylisobutylate) (radical polymerization initiator, 83 parts), N,N'-dimethylformamide (900 parts) and methyl amyl ketone (900 parts) were placed in another vessel and then stirred to prepare a monomer solution. The obtained solution was purged with nitrogen gas for 30 minutes.

The monomer solution was then introduced into the reaction vessel for 2 hours by means of a peristaltic pump. After the introduction was completed, the reaction mixture was kept at 120° C. for 4 hours.

After cooled to room temperature, the mixture was poured into n-heptane (15000 parts). The top clear portion was then removed, and the left reaction mixture was dissolved in tetrahydrofuran (2000 parts). The obtained solution was poured into water (15000 parts) to form white precipitates. The precipitates were isolated by filtration under reduced pressure, and dried overnight in a vacuum oven at 50° C.

As a result of drying, AMMA/MAA (20/80) copolymer (Polymer P4) in an amount of 780 parts (yield: 96%) was obtained in the form of white powder. The molecular weight of the product was measured by means of GPC (THF), to find that the product had a weight average molecular weight Mw of 6389 Da, a number average molecular weight Mn of 2159 Da and a polydispersity index PDI of 2.96.

Polymer Synthesis Example 5

Synthesis of PQMA/MAdMA (75/25) Copolymer (Polymer P5)

In a reaction vessel equipped with a stirrer, a condenser, a heater and a thermostat, methyl amyl ketone (MAK, 100 parts) as a solvent was placed and purged with nitrogen gas for 30 minutes, and then heated to 120° C.

Independently, 4-hydroxyphenyl methacrylate (PQMA, 189 parts), 2-methyladamantane-2-yl methacrylate (MAdMA, 83 parts), dimethyl 2,2'-azobis(2-methylisobutylate) (radical polymerization initiator, 27 parts) and methyl amyl ketone (MAK, 600 parts) were placed in another vessel and then stirred to prepare a monomer solution. The obtained solution was purged with nitrogen gas for 30 minutes.

The monomer solution was then introduced into the reaction vessel for 2 hours by means of a peristaltic pump. After the introduction was completed, the reaction mixture was kept at 120° C. for 4 hours.

After cooled to room temperature, the mixture was poured into n-heptane (5000 parts). The top clear portion was then removed, and the left reaction mixture was dissolved in tetrahydrofuran (700 parts). The obtained solution was poured into n-heptane (5000 parts) to form white precipitates. The precipitates were isolated by filtration under reduced pressure, and dried overnight in a vacuum oven at 50° C.

As a result of drying, PQMA/MAdMA (75/25) copolymer (Polymer P5) in an amount of 280 parts (yield: 93%) was obtained in the form of white powder. The molecular weight of the product was measured by means of GPC (THF), to find that the product had a weight average molecular weight Mw of 6389 Da, a number average molecular weight Mn of 3227 Da and a polydispersity index PDI of 1.98.

Polymer Synthesis Example 6

Synthesis of HNMA/AMMA/OTMA (60/25/15) Terpolymer (Polymer P6)

In a 250 mL round-bottom flask equipped with a magnetic stirrer, a condenser, a nitrogen gas inlet and a thermostat, 135 g of propyleneglycol monomethyl ether acetate (PGMEA) solvent was placed and purged with nitrogen gas for 30 minutes. The deaerorated solvent was then heated at 80° C. by means of a heating mantle. Independently, 16.7 g of 9-hydroxynaphthyl methacrylate (HNMA), 3.4 g of oxathianyl methacrylate (OTMA), 8.43 g of 9-anthracenemethyl methacrylate (AMMA), 1.44 g of azobis(isobutyronitrile) (AIBN) initiator and 135 g of PGMEA were mixed and purged with nitrogen gas for 30 minutes, to prepare a deaerated PGMEA solution. The obtained PGMEA solution was dropwise added over a period of 3 hours into the above heated solvent from a pressure equalizing dropping funnel. The reaction mixture was further kept heated at 80° C. for 3 hours, to promote the polymerization. Thereafter, the reaction mixture was cooled to room temperature under nitrogen atmosphere. When the temperature of the mixture reached down to 30° C., 4.5 g of methanol was added so as to terminate the reaction. The obtained PGMEA solution was poured into twice volumes of hexane, to precipitate the polymer. The precipitated polymer (Polymer P6) was collected and washed three times with a mixture of water and methanol, and then dried in a vacuum oven at 40° C. for 48 hours.

Application Example 1

To Polymer P1 (61 parts), the cross-linking agent C1 (7 parts), triphenylsulfonium salt (hereinafter, referred to as "TPS", 9 parts), propyleneglycol monomethyl ether acetate (956 parts), propyleneglycol monomethyl ether (1867 parts) and ethyl lactate (57 parts) were added. The obtained mixture was stirred at room temperature for 30 minutes, to prepare a composition for forming a bottom anti-reflective coating.

The prepared composition for forming a bottom anti-reflective coating was cast by spin-coating on a silicon microchip wafer, and crosslinked by heating at 190° C. for 60 seconds on a vacuum hot-plate, to obtain a bottom anti-reflective coating. The obtained coating was measured by means of ellipsometer, and it was found that the refractive index (n value) and the extinction coefficient (k value) at 248 nm were 1.54 and 0.46, respectively. The refractive index (n value) and the extinction coefficient (k value) at 193 nm were also found to be 1.91 and 0.47, respectively.

Independently, the above procedure was repeated and the composition was heated at 190° C. to form a bottom anti-reflective coating. It was verified that the formed coating was insoluble in any of ethyl lactate, propyleneglycol monomethyl ether acetate and propyleneglycol monomethyl ether.

Successively, on the obtained bottom anti-reflective coating, a commercially available 248 nm positive-working photoresist was spin-coated. The formed resist layer was subjected to soft-baking at 120° C. for 60 seconds on a vacuum hot-plate and then imagewise exposed to radiation of 248 nm through a photomask. After subjected to post-exposure baking 130° C. for 60 seconds, the resist layer was developed with a 2.38 wt % TMAH aqueous solution. As a result of this development, both of the photoresist layer and the underlying bottom anti-reflective coating were removed in the area demarcated by the photomask. In the area exposed to radiation, the anti-reflective coating was dissolved together with the photoresist and any residue of the coating was not observed. The formed pattern had a cross section in which both of the photoresist and the bottom anti-reflective coating showed rectangular side-faces perpendicular to the substrate surface. Further, scum was not observed to be formed from the bottom anti-reflective coating.

Independently, on the obtained bottom anti-reflective coating, a commercially available 193 nm positive-working photoresist was spin-coated. The formed resist layer was subjected to soft-baking at 120° C. for 60 seconds on a vacuum hot-plate and then imagewise exposed to radiation of 193 nm through a photomask. After subjected to post-exposure baking 130° C. for 60 seconds, the resist layer was developed with a 2.38 wt % TMAH aqueous solution. As a result of this development, both of the photoresist layer and the underlying bottom anti-reflective coating were removed in the area demarcated by the photomask. In the area exposed to radiation, the anti-reflective coating was dissolved together with the photoresist and any residue of the coating was not observed. The formed pattern had a cross section in which both of the photoresist and the bottom anti-reflective coating showed rectangular side-faces perpendicular to the substrate surface. Further, scum was not observed to be formed from the bottom anti-reflective coating.

Application Examples 2 to 12 and Application Comparative Examples 1 and 2

The procedure of Application example 1 was repeated except that the components of the composition for forming a bottom anti-reflective coating were changed into those shown in Table 1, to prepare and evaluate compositions of Application examples 2 to 12 and Application comparative examples 1 and 2. In Application comparative examples 1 and 2, tris((4-vinyloxy)butyl)cyclohexane-1,2,4-tricarboxylate (hereinafter, referred to as "CA") and tris((4-vinyloxy)-butyl)benzene-1,2,4-tricarboxylate (hereinafter, referred to as "CB"), respectively, were used as the cross-linking agents. The results were shown in Table 1.

TABLE 1

| | | | | Optical characteristics | | | | | Development characteristics | | | |
| | | | | 248 nm | | 193 nm | | | 248 nm resist | | 193 nm resist | |
| | Polymer | Cross-linking agent | Photo acid generator | refractive index n | extinction coefficient k | refractive index n | extinction coefficient k | solvent resistance | sectional shape of pattern | scum | sectional shape of pattern | scum |
|---|---|---|---|---|---|---|---|---|---|---|---|---|
| Appli. ex. | | | | | | | | | | | | |
| 1 | P1 | C1 | TPS | 1.54 | 0.46 | 1.91 | 0.47 | A | A | A | A | A |
| 2 | P1 | C1 | — | 1.52 | 0.48 | 1.89 | 0.45 | A | A | A | A | A |
| 3 | P1 | C2 | TPS | 1.53 | 0.45 | 1.91 | 0.46 | A | A | A | A | A |
| 4 | P1 | C3 | TPS | 1.54 | 0.46 | 1.91 | 0.47 | B | A | B | A | B |
| 5 | P1 | C4 | TPS | 1.56 | 0.49 | 1.88 | 0.43 | B | A | B | A | B |
| 6 | P1 | C5 | TPS | 1.56 | 0.43 | 1.90 | 0.48 | A | A | A | A | A |
| 7 | P2 | C1 | TPS | 1.52 | 0.45 | 1.93 | 0.48 | A | A | A | A | A |
| 8 | P3 | C1 | TPS | 1.55 | 0.43 | 1.95 | 0.49 | A | A | A | A | A |
| 9 | P4 | C1 | TPS | 1.58 | 0.44 | 1.46 | 0.65 | A | A | A | A | A |
| 10 | P5 | C1 | TPS | 1.73 | 0.15 | 1.80 | 0.54 | A | A | A | A | A |
| 11 | P6 | C1 | TPS | 1.55 | 0.43 | 1.95 | 0.49 | A | A | A | A | A |
| Appli. com. ex. | | | | | | | | | | | | |
| 1 | P1 | CA | TPS | 1.54 | 0.43 | 1.61 | 0.52 | A | C | C | C | C |
| 2 | P1 | CB | TPS | 1.54 | 0.43 | 1.61 | 0.52 | A | C | C | C | C |

Evaluation Criteria

Solvent Resistance

A: the bottom anti-reflective coating was insoluble in any of ethyl lactate, propyleneglycol monomethyl ether acetate and propyleneglycol monomethyl ether;

B: the bottom anti-reflective coating was slightly soluble in ethyl lactate, propyleneglycol monomethyl ether acetate or propyleneglycol monomethyl ether, but was practically usable without any trouble; and C: the bottom anti-reflective coating was soluble in one or all of ethyl lactate, propyleneglycol monomethyl ether acetate and propyleneglycol monomethyl ether, and was of no practical use.

Cross-Sectional Shape of Pattern

A: both of the photoresist and the bottom anti-reflective coating showed rectangular side-walls perpendicular to the substrate surface;

B: both of the photoresist and the bottom anti-reflective coating showed side-walls not perpendicular but slightly inclined to the substrate surface, but were practically usable without any trouble; and C: both of the photoresist and the bottom anti-reflective coating showed side-walls in fitting shapes to the substrate surface.

Scum

A: scum was not observed to be formed from the bottom anti-reflective coating;

B: scum was slightly observed to be formed from the bottom anti-reflective coating, but was practically negligible; and C: scum was considerably observed to be formed from the bottom anti-reflective coating.

The invention claimed is:

1. A cross-linking agent represented by the following formula (1):

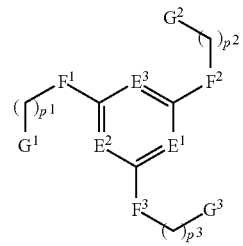

(1)

wherein each of $E^1$ to $E^3$ is independently selected from the group consisting of carbon and nitrogen atoms, provided that at least one of them is a nitrogen atom;

each of $F^1$ to $F^3$ is independently selected from the group consisting of oxygen and sulfur atoms;

each of $G^1$ to $G^3$ is independently selected from the group consisting of a vinyloxy group, a N-methoxymethylamide group and a hydrogen atom, provided that at least one of them is a vinyloxy group or a N-methoxymethylamide group; and each of $p^1$ to $p^3$ is independently selected from integer including 0 provided that at least any two of them are at least 1 or above 1.

2. The cross-linking agent according to claim 1, wherein all of $E^1$ to $E^3$ are nitrogen atoms.

3. The cross-linking agent according to claim 1, wherein two of $E^1$ to $E^3$ are nitrogen atoms.

4. The cross-linking agent according to claim 1, wherein one of $E^1$ to $E^3$ is nitrogen atom.

5. The cross-linking agent according to claim 1, wherein $F^1$ to $F^3$ are oxygen atoms.

6. The cross-linking agent according to claim 1, wherein $F^1$ to $F^3$ are sulfur atoms.

7. The cross-linking agent according to claim 1, wherein $G^1$ to $G^3$ are vinyloxy groups.

8. The cross-linking agent according to claim 1, wherein $G^1$ to $G^3$ are N-methoxymethylamide groups.

9. A process for preparing the cross-linking agent of claim 1, characterized in that
a compound represented by the following formula (2):

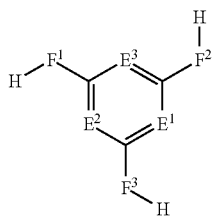
(2)

wherein each of $E^1$ to $E^3$ is independently selected from the group consisting of carbon and nitrogen atoms, provided that at least one of them is a nitrogen atom; and each of $F^1$ to $F^3$ is independently selected from the group consisting of oxygen and sulfur atoms
and
a compound represented by the following formula (3):

(3)

wherein X is selected from the group consisting of chlorine, bromine and iodine atoms; G is a vinyloxy group or a N-methoxymethylamide group;
and p is an integer of 0 or more
are made to react with a basic compound.

10. A composition for forming a bottom anti-reflective coating, comprising;
a solvent,
the cross-linking agent according to claim 1, and
a polymer.

11. The composition of claim 10, where the polymer is represented by the following formula (4):

$-A_m-B_n-$ (4)

wherein
A and B are repeating units represented by the following formulas (A) and (B), respectively;

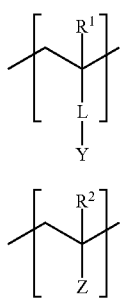

in which
each of $R^1$ and $R^2$ is independently a group selected from the group consisting of a hydrogen atom and alkyl groups;
L is a linking group selected from the group consisting of a single bond, straight-chain and branched chain alkylene groups having one or more carbon atoms, and COO;
Y is an aromatic group containing one or more benzene rings, provided that the aromatic group may or may not have a substituent selected from the group consisting of, alkyl, aryl, halogen atoms, alkoxy, nitro, aldehyde, cyano, amide, dialkylamino, sulfonamide, imide, carboxy, carboxylic acid ester, sulfo, sulfonic acid ester, alkylamino, and arylamino, and also provided that one of the benzene rings contained in the aromatic group may be replaced with a quinone ring; and
Z is a group selected from the group consisting of $R^3COOR^4$ and $R^3OR^4$, in which $R^3$ is a group selected from the group consisting of single bond, oxygen atom, aromatic ring, and straight-chain and branched chain alkylene groups which have one or more carbon atoms and which may be substituted with a fluorine atom, and also in which $R^4$ is a group selected from the group consisting of a hydrogen atom, substituted hydrocarbon groups and non-substituted hydrocarbon groups;
the repeating units A and B may be connected either randomly or to form a block,
each of the repeating units A and B may be a combination of two or more repeating units having different structures, and
m and n are numbers indicating polymerization degrees, and are a number of 10 or more and a number of 0 or more, respectively.

12. The composition according to claim 10 for forming a bottom anti-reflective coating, further comprising a photo acid generator.

13. A bottom anti-reflective coating obtained by casting onto a substrate the composition according to claim 10 for forming a bottom anti-reflective coating, and then heating it.

14. A pattern formation method comprising:
casting the composition according to claim 10 for forming a bottom anti-reflective coating onto a semiconductor substrate, and then baking it to form a bottom anti-reflective coating;
forming a photoresist layer on the bottom anti-reflective coating;
subjecting to light exposure the semiconductor substrate covered with the bottom anti-reflective coating and the photoresist layer; and
developing the exposed substrate with a developing solution: thereby forming a pattern in the bottom anti-reflective coating.

15. The pattern formation method according to claim 14, wherein the exposure is carried out by use of light in the wavelength range of 13.5 to 248 nm.

* * * * *